United States Patent [19]

Schamper et al.

[11] Patent Number: 4,518,582

[45] Date of Patent: May 21, 1985

[54] ACID STABLE DIBENZYL MONOSORBITOL ACETAL GELS

[75] Inventors: Thomas J. Schamper, Ramsey, N.J.; Martin M. Perl, Brooklyn; James D. Warren, Pearl River, both of N.Y.

[73] Assignee: American Cyanamid Co., Stamford, Conn.

[21] Appl. No.: 501,462

[22] Filed: Jun. 6, 1983

Related U.S. Application Data

[63] Continuation-in-part of Ser. No. 373,590, Apr. 30, 1982, abandoned.

[51] Int. Cl.$^3$ .................. A61K 7/32; A61K 7/34; A61K 7/38
[52] U.S. Cl. .................. 424/66; 424/DIG. 5; 424/65; 424/68
[58] Field of Search .................. 424/66, DIG. 5

[56] References Cited

U.S. PATENT DOCUMENTS

| | | | |
|---|---|---|---|
| 4,264,586 | 4/1981 | Callingham | 424/68 |
| 4,265,878 | 5/1981 | Reil | 424/68 |
| 4,268,499 | 5/1981 | Reil | 424/68 |
| 4,346,079 | 8/1982 | Roehl | 424/DIG. 5 |
| 4,350,605 | 9/1982 | Hughett | 424/68 |

Primary Examiner—Dale R. Ore
Attorney, Agent, or Firm—Charles J. Fickey

[57] ABSTRACT

Antiperspirant stick compositions containing dibenzyl monosorbitol acetal in the presence of acidic antiperspirant-active salts, which are stable for extended periods of time at elevated temperatures; said sticks comprising (a) about 1 to 80 percent by weight of a reactive solvent; (b) about 0 to 75 percent by weight of a non-reactive solvent; (c) about 1 to 10 percent by weight of dibenzyl monosorbitol acetal; (d) about 0 to 35 percent by weight of an emollient; (e) about 5 to 25 percent by weight of an antiperspirant-active compound; (f) about 0 to 2.5 percent by weight of a $C_{12}$–$C_{20}$ fatty acid; and (g) 0.05 to 15 percent by weight of a gel stabilizer; said gel stabilizer being a member of the group consisting of magnesium sulfate, zinc acetate and hexamethylenetetramine and mixtures thereof.

7 Claims, No Drawings

ACID STABLE DIBENZYL MONOSORBITOL ACETAL GELS

This is a continuation-in-part of copending application Ser. No. 373,590 filed Apr. 30, 1982, now abandoned.

The present invention relates to gelled cosmetic sticks in general. More particularly, it relates to gelled antiperspirant sticks containing an acidic antiperspirant-active compound. Still more particularly, it relates to antiperspirant sticks containing an acidic antiperspirant-active compound in the presence of dibenzyl monosorbitol acetal (DBMSA) as the gelling agent, and to a method for the stabilization of said sticks against deterioration.

Many known cosmetic sticks consist largely of gelled alcoholic solutions. Sticks which exhibit a desirable transparent or translucent appearance are readily prepared using sodium stearate as the gelling agent: however, they cannot be prepared in the presence of acidic antiperspirant-active salts because the alkaline gelling agent will react with the salt. Opaque sticks are readily prepared from acidic antiperspirant salts using certain low melting waxy materials, such as stearyl alcohol. The sticks are stable, but there is a need for a method of making acid-stable, translucent antiperspirant sticks, particularly using dibenzyl monosorbitol acetal as the gelling agent.

Dibenzyl monosorbitol acetal is a unique gelling agent, providing translucent sticks. No derivative of sorbitol or any other gelling agent has yet been found which provides sticks having equal properties. Dibenzyl monosorbitol acetal has been known for a long time. However, it is also known that acetals are stable in alkaline or neutral media, but not in acidic media. In an acidic environment even in the presence of small amounts of water, the acetal hydrolyzes; or it will react with a reactive alcohol, e.g. ethanol, to form a different acetal.

Thus, antiperspirant sticks containing acidic antiperspirant-active compounds in the presence of dibenzyl monosorbitol acetal in reactive alcoholic solvents have not been satisfactory because, in time, especially at elevated temperatures, they deteriorate and liquify. There is a need, therefore, to find a way to stabilize these sticks against such deterioration.

Antiperspirant sticks containing dibenzyl monosorbitol acetal and acidic antiperspirant-active salts are disclosed by Roehl, U.S. Pat. No. 4,154,816 (Naarden). These sticks contain, in addition to the salt and gelling agent, a lower monohydric alcohol, such as ethanol; a di- or trihydric alcohol, such as 1,2-propylene glycol or 1,3-butylene glycol, and/or a lower polyglycol; a propylene-/ethylene glycol polycondensate, having the formula:

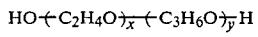

wherein $y/x+y = 0.6-1$ and an average molecular weight of at least 500; and optionally, a mono- or dialkanolamide of a higher ($C_8$–$C_{20}$) fatty acid, such as N-(2-hydroxyethyl)cocamide.

In British application No. 2,062,466, Roehl discloses that a drawback to the sticks described above is their stickiness on application, which can be eliminated by entirely omitting, or greatly reducing, the polycondensate, and adding instead about 0 to 25 percent by weight of an oleaginous compound for stickiness control.

Applicants have found that the antiperspirant sticks described by Roehl are not stable on extended exposure at an elevated temperature.

In accordance with the present invention there is provided antiperspirant sticks containing dibenzyl monosorbitol acetal in the presence of acidic antiperspirant-active salts, which are stable for extended periods of time at elevated temperatures; said sticks comprising (a) about 1 to 80 percent by weight of a reactive solvent; (b) about 0 to 75 percent by weight of a non-reactive solvent; (c) about 1 to 10 percent by weight of dibenzyl monosorbitol acetal; (d) about 0 to 35 percent by weight of an emollient; (e) about 5 to 25 percent by weight of an antiperspirant-active compound; (f) about 0 to 2.5 percent by weight of a $C_{12}$–$C_{20}$ fatty acid; and (g) 0.05 to 15 percent by weight of a gel stabilizer; said gel stabilizer being a member of a group consisting of magnesium sulfate, zinc acetate and hexamethylenetetramine and mixtures thereof.

Reactive solvents are defined as water, methanol, ethanol, n-propanol, n-butanol, 2-methoxyethanol, 2-ethoxyethanol; ethylene glycol, 1,2-propylene glycol, 1,3-propylene glycol, 1,4-butylene glycol, 1,2-butylene glycol, diethylene glycol, and the like, and mixtures thereof. These solvents, because they are primary alcohols or because of their low molecular weight, tend to be more reactive towards dibenzyl monosorbitol acetal in the presence of acidic antiperspirant-active salts. They are, however, excellent solvents for the preparation of the gelled sticks, particularly ethanol. There use, however, should be the least amount consistent with the preparation of useful sticks. Generally, their useful range is from about 5 to 65 percent by weight.

Non-reactive solvents, as defined herein, are those which, because of the presence of less reactive secondary alcohol groups or because of their chain length, are less reactive towards dibenzyl monosorbitol acetal in the presence of acidic antiperspirant-active salts. These solvents include isopropanol, isobutanol, diethylene glycol monomethylether, diethylene glycol monoethyl ether, 1,3-butylene glycol, 2,3-butylene glycol, dipropylene glycol, 2,4-dihydroxy-2-methylpentane, and the like, and mixtures thereof.

Because of their lower reactivity towards dibenzyl monosorbitol acetal their usage is preferably maximized, consistent with the preparation of useful sticks. A generally useful range is about 10 to 70 percent by weight of the stick composition.

The preferred reactive solvent is ethanol, either anhydrous or containing up to about 5 percent water. The preferred non-reactive solvents are 1,3-butylene glycol and 2,4-dihydroxy-2-methylpentane (sometimes referred to as hexylene glycol) and mixtures thereof.

Sticks containing dibenzyl monosorbitol acetal in the presence of acidic antiperspirant-active salts do not have adequate long term stability, especially at elevated temperatures, when the solvent, or mixture of solvents, used in their preparation, comprises a significant amount of a reactive solvent. Stability, as used herein, means the time it took for the stick to completely liquify. Thus, the stick compositions of the present invention require stabilization against deterioration especially at elevated temperatures and are so stabilized by the incorporation therein of one or more of the gel stabilizers described above. The particular reactive solvent and/or the particular less reactive solvent used, and the relative proportions of each, will result in sticks requiring relatively more or less stabilizer.

The stabilizers useful in the present invention to prevent or retard deterioration of the gelled sticks, especially when exposed to elevated temperatures, include magnesium sulfate, zinc acetate, and hexamethylenetetramine, and mixtures thereof. One or a combination of these stabilizers may be used in the stick compositions of the invention. The amount of stabilizers required will vary and will depend on the relative instability inherent in the solvents used, their relative proportions, and on the acidity of the antiperspirant-active salt used. The magnesium sulfate and zinc acetate stabilizers ordinarily will be used in an amount ranging from about 0.2 to 2 percent by weight, preferably about 0.5 to 1 percent by weight, and hexamethylenetetramine ordinarily will be used in an amount ranging from about 0.05 to 0.5 percent by weight, preferably about 0.1–0.2 percent by weight. In general, however, the stabilizer or combination of stabilizers will be used in an amount ranging from about 0.05 to 15 percent by weight, based on the total weight of the stick.

In addition to the solvents, dibenzyl monosorbitol acetal, antiperspirant-active salt and stabilizer, the sticks may contain other commonly used ingredients.

A liquid, volatile cyclic dimethylsiloxane may be added to the composition to provide a desirable dry feel and emolliency. Other commonly used emollients, such as PPG-3 myristyl ether, and the like, may be incorporated into the stick either in place of or in addition to the dimethylsiloxane. Although optional, it is preferred to use about 3 to 30 percent by weight of one or a combination of emollients.

The antiperspirant-active metal salts used in the present invention are the usual aluminum and/or zirconium compounds, especially aluminum hydroxy chlorides. They may be added in the form of a complex to enhance solubility in alcohols, such as aluminum chlorohydrex or Al/Zr chlorohydrex. The metal salts are effectively used in an amount 10 to 20 percent by weight.

When solutions of aluminum hydroxychlorides are heated there is a tendency towards premature gelation. This may be suppressed by the addition of a small amount of a $C_{12}$–$C_{18}$ fatty acid, such as stearic acid, without adversely affecting the stability of the gel.

In addition to the ingredients described above, the antiperspirant sticks may contain other ingredients in minor amount, such as a dye color or a fragrance.

The following examples illustrate the invention.

EXAMPLES 1–5

The following antiperspirant sticks were prepared and then exposed at a temperature of 45° C. to determine their stability.

| Ingredient | Parts by weight | | | |
|---|---|---|---|---|
| | 1 | 2 | 3 | 4 |
| 1,3-Butylene glycol | 25.0 | 25.0 | 25.0 | 25.0 |
| 2,4-dihydroxy-2-methylpentane | 3.0 | 3.0 | 3.0 | 3.0 |
| Ethanol (anhydrous) | 47.3 | 47.2 | 46.8 | 46.8 |
| Steareth 100[1] | 1.0 | 1.0 | 1.0 | 1.0 |
| DBMSA | 3.0 | 3.0 | 3.0 | 3.0 |
| Aluminum Chlorohydrex | 15.0 | 15.0 | 15.0 | 15.0 |
| Cyclomethicone | 5.0 | 5.0 | 5.0 | 5.0 |
| Stearic acid | 0.5 | 0.5 | 0.5 | 0.5 |
| Hydroxypropyl cellulose | 0.2 | 0.2 | 0.2 | 0.2 |
| Stabilizer | | | | |
| Hexamethylenetetramine | — | 0.1 | — | — |
| Magnesium sulfate | — | — | 0.5 | — |
| Zinc acetate | — | — | — | 0.5 |
| Stability at 45° C., weeks | 5–6 | 27 | 12 | 27 |

[1] Ethoxylated stearyl alcohol

EXAMPLES 6–13

The following antiperspirant sticks were prepared and then exposed at 60° C. to determine their stability.

| Ingredient | Parts by weight | | | |
|---|---|---|---|---|
| | 5 | 6 | 7 | 8 |
| 1,3-Butylene glycol | 20.0 | 20.0 | 20.0 | 20.0 |
| 2,4-Dihydroxy-2-methylpentane | 10.0 | 10.0 | 10.0 | 10.0 |
| Ethanol (anhydrous) | 50.3 | 49.7 | 49.9 | 49.9 |
| Steareth 100 | 1.0 | 1.0 | 1.0 | 1.0 |
| DBMSA | 3.0 | 3.0 | 3.0 | 3.0 |
| Aluminum Chlorohydrex | 10.0 | 10.0 | 10.0 | 10.0 |
| Cyclomethicone | 5.0 | 5.0 | 5.0 | 5.0 |
| Stearic acid | 0.5 | 0.5 | 0.5 | 0.5 |
| Hydroxypropyl cellulose | 0.2 | 0.2 | 0.2 | 0.2 |
| Stabilizer | | | | |
| Hexamethylenetetramine | — | — | 0.1 | 0.1 |
| Magnesium sulfate | — | 0.3 | 0.3 | — |
| Zinc acetate | — | 0.3 | — | 0.3 |
| Stability at 60° C., Days | 2 | 21 | 32 | 56 |

We claim:

1. A solid transparent, gelled antiperspirant composition comprising:
   (a) 1 to 80 percent by weight of a reactive solvent;
   (b) 0 to 75 percent by weight of a non-reactive solvent;
   (c) 1 to 10 percent by weight of dibenzyl monosorbitol acetal;
   (d) 0 to 35 percent by weight of an emollient;
   (e) 5 to 25 percent by weight of an acidic antiperspirant-active metal salt;
   (f) 0 to 2.5 percent by weight of a $C_{12}$ to $C_{20}$ fatty acid; and
   (g) 0.05 to 15 percent by weight of a gel stabilizer selected from the group consisting of magnesium sulfate, zinc acetate and hexamethylenetetramine, and mixtures thereof.

2. A composition according to claim 1 where (a) is ethanol and (b) is 1,3-butylene glycol or 2,4-dihydroxy-2-methylpentane or a mixture thereof.

3. A composition according to claim 1 wherein the acidic antiperspirant active metal salt is aluminum chlorhydrex or aluminum/zirconium chlorhydrex.

4. A method for stabilizing an antiperspirant stick composition comprising reactive alkanols, and optionally non-reactive alkanols, an antiperspirant active metal salt, and dibenzyl monosorbitol acetal, which comprises adding to said composition a compound selected from the group consisting of magnesium sulfate, zinc acetate and hexamethylenetetramine, and mixtures thereof.

5. A method according to claim 4 wherein said reactive alkanol is ethanol.

6. A method according to claim 4 wherein said non-reactive alkanol is 1,3-butylene glycol or 2,4-dihydroxy-2-methylpentane or a mixture thereof.

7. A method according to claim 4 wherein the active metal salt is aluminum chlorhydrex or aluminum/zirconium chlorhydrex.

* * * * *